United States Patent [19]

Adams

[11] 3,932,650

[45] Jan. 13, 1976

[54] TRANS-OCTAHYDROPYRIDOINDOLOBENZAZEPINES AS CENTRAL NERVOUS SYSTEM DEPRESSANTS

[75] Inventor: Charles De Witt Adams, Wilmington, Del.

[73] Assignee: E. I. Du Pont de Nemours & Company, Wilmington, Del.

[22] Filed: Dec. 6, 1973

[21] Appl. No.: 422,616

Related U.S. Application Data

[63] Continuation-in-part of Ser. No. 325,352, Jan. 22, 1973.

[52] U.S. Cl............................ 424/267; 260/239.55
[51] Int. Cl.².................................... A61K 31/445
[58] Field of Search................ 424/267; 260/293.55

[56] References Cited

UNITED STATES PATENTS

3,373,168   3/1968   Cohen et al. .................... 260/293

*Primary Examiner*—Stanley J. Friedman

[57] ABSTRACT

Certain 3-substituted octahydropyridoindolobenzazepines and their addition salts with pharmaceutically acceptable acids produce a marked central nervous system depressant activity in warm-blooded animals. These compounds are stereoisomers of prior art 3-substituted octahydropyridoindolobenzazepines which have a central nervous system antidepressant activity.

4 Claims, No Drawings

TRANS-OCTAHYDROPYRIDOINDOLOBENZAZEPINES AS CENTRAL NERVOUS SYSTEM DEPRESSANTS

CROSS REFERENCE TO RELATED APPLICATION

This application is a continuation-in-part of application Ser. No. 325,352, filed Jan. 22, 1973.

BACKGROUND OF THE INVENTION

This invention relates to novel octahydropyridoindolobenzazepines, which are useful as central nervous system depressants.

Certain octahydropyridoindolobenzazepines are known from U.S. Pats. 3,373,153; 3,373,154; 3,373,168; and 3,457,271, all assigned to Hoffmann-La Roche, Inc. Those compounds can be represented according to the above-mentioned patents by the following formula (1):

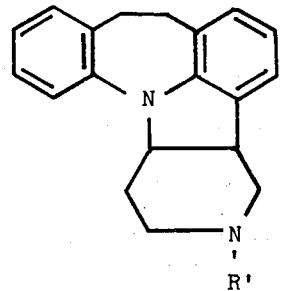

(1)

wherein R' is a straight chain or branched alkyl having 1-7 carbon atoms.

The compounds of Formula (1) are said in Pat. Nos. 3,373,168 and 3,457,271 to have antidepressant activity and to be useful antidepressant agents. These compounds are prepared according to the above two patents by reduction of the corresponding hexahydro compounds either with sodium in a mixture of tetrahydrofuran and liquid ammonia or with zinc in hydrochloric acid. The former method is preferred by the patentees since it gives higher yields.

None of the above patents nor any other reference known to applicant suggests that octahydropyridoindolobenzazepines such as those of the Hoffmann-La Roche patents may have central nervous system depressant properties.

SUMMARY OF THE INVENTION

It has now been discovered that certain novel octahydropyridoindolobenzazepines and their addition salts with pharmaceutically acceptable organic or inorganic acids are useful central nervous system (hereafter, CNS) depressant agents. These novel compounds will be represented according to the IUPAC 1957 Rules as follows:

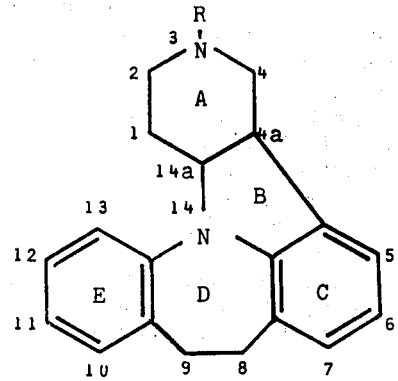

(2)

In the above Formula (2), R stands for benzyl; benzyl ring-substituted with methyl, methoxy or chloro; phenethyl; 3-phenylpropyl; 3-phenylpropyl ring substituted with chloro, bromo or methoxy; furfuryl; 2-thenyl; $C_1$-$C_5$ alkyl; cyclopropyl; $C_4$-$C_8$ cycloalkylmethyl; (methylcyclopropyl)methyl; exo-7-norcarylmethyl; (4-methylbicyclo[2.2.2]oct-1-yl)methyl; (bicyclo[2.2.1]hept-2-yl)methyl; 1-adamantylmethyl or 2-adamantylmethyl.

The E and D rings in FIG. (2) form the benzazepine portion of the molecule; rings B and C form the indolo portion; and ring A forms the pyrido portion. It is believed that the compounds of the present invention have the trans-configuration of the 4a and 14a hydrogens, and that the prior art compounds disclosed in the above-cited patents have the cis-configuration of those hydrogen atoms.

The compounds of the present invention also have analgesic activity in warm-blooded animals.

DETAILED DESCRIPTION OF THE INVENTION

The compounds of the present invention are prepared by the reduction of the corresponding hexahydro compounds (3) with boron hydride in tetrahydrofuran. This reaction is illustrated by the following equation:

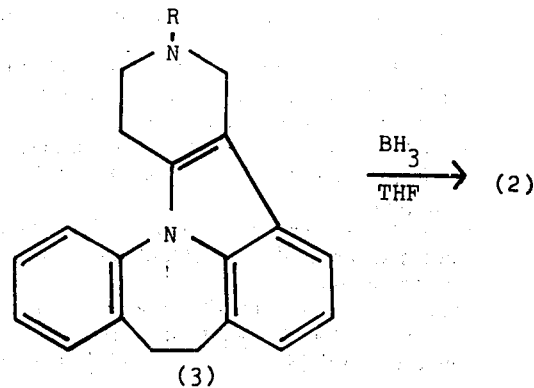

(3) → (2)

where R is benzyl; benzyl ring-substituted with methyl, methoxy or chloro; phenethyl; 3-phenylpropyl; 3-phenylpropyl ring substituted with chloro, bromo or methoxy; furfuryl; 2-thenyl; $C_1$-$C_5$ alkyl; cyclopropyl; $C_4$-$C_8$ cycloalkylmethyl; (methylcyclopropyl)methyl; exo-7-norcarylmethyl; (4-methylbicyclo[2.2.2]oct-1-yl)methyl; (bicyclo[2.2.1]hept-2-yl)methyl; 1-adamantylmethyl or 2-adamantylmethyl.

The preparation of most compounds of this invention can also start with the corresponding 3-acyl compounds, provided an excess boron hydride is used to reduce the amide carbonyl to a methylene and the 4a – 14a double bond to a single bond. This reaction is shown below:

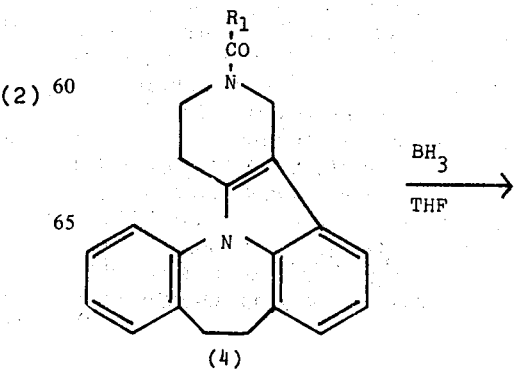

(4)

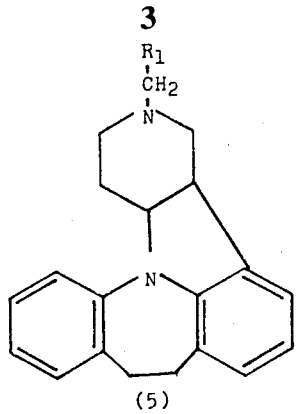

(5)

where $R_1$—$CH_2$— corresponds to R as previously defined excluding cyclopropyl. $R_1$ thus can be, for example, hydrogen, methyl, ethyl, propyl, isopropyl, cyclopropyl, cyclopentyl, exo-7-norcaryl, or phenyl.

According to the 1957 IUPAC Rules, representative compounds within the scope of Formula (2) (disregarding their steric configuration) will be named as follows:

When R = methyl: 1,2,3,4,4a, 8.9.14a-octahydro-3-methylpyrido[4',3':2,3]indolo[1,7-ab][1]benzazepine;

when R = ethyl: 3-ethyl-1,2,3,4,4a, 8,9,14a-octahydropyrido[4',3':2,3]indolo[1,7-ab][1]benzazepine;

when R = cyclopropylmethyl: 3-(cyclopropylmethyl)-1,2,3,4,4a,8,9,14a-octahydropyrido[4',3':2,-3]indolo[1,7-ab][1]benzazepine;

when R = isobutyl: 1,2,3,4,4a,8,9,14a-octahydro-3-isobutylpyrido[4',3':2,3]indolo[1,7-ab][1]benzazepine;

when R = benzyl: 3-benzyl-1,2,3,4,4a,8,9,14a-octahydropyrido[4',3':2,3]indolo[1,7-ab][1]benzazepine; and when R = exo-7-norcarylmethyl: trans-1,2,3,4,4a,8,9,14a-Octahydro-3-(exo-7-norcarylmethyl)pyrido[4',3':2,3]indolo[1,7-ab][1]benzazepine The starting materials for the preparation of the compounds of the present invention, the corresponding hexahydropyridoindolobenzazepines can be made, for example, by the method disclosed in the above-cited Hoffman-La Roche U.S. patents; namely, by N-nitrosating iminodibenzyl, reducing the product to N-aminoiminodibenzyl, condensation with an appropriately substituted 4-piperidinone, and cyclization with an acid. The methyl- and ethyl-substituted hexahydropyridoindolobenzazepines are prior art compounds; several other 3-substituted hexahydropyridoindolobenzazepines are described in U.S. Pat. 3,764,684 of Michael Finizio, issued Oct. 9, 1973 on Ser. No. 170,990, filed Aug. 11, 1971.

The reduction of the hexahydro precursors to the octahydro compounds is best carried out with a four- to five-fold excess of boron hydride/tetrahydrofuran complex at a temperature as low as 0°C or as high as the reflux temperature of tetrahydrofuran. The reducing power of the boron hydride/tetrahydrofuran reagent may be further enhanced by dilution with a higher-boiling ether, for example, diglyme, which allows the reaction to be conducted at a higher temperature, usually not over 100°-110°C. The reaction mixture is then acidified with about 4-10 molar hydrochloric acid, heated to 100°C., allowed to cool, and neutralized with caustic. The product can be recovered in any suitable manner, including extraction, evaporation followed by extraction, conversion to an addition salt, etc.

The carbonyl compounds useful in the process of this invention, represented by the above Formula (4), can be made from the 3-unsubstituted compound by reaction with an appropriate acylating agent, which may be represented by the following Formula (5)

 (5)

wherein X is a halogen, a $C_1$-$C_4$ alkoxy group,

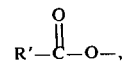

or

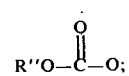

R' being the same as $R_1$ or a $C_1$-$C_4$ alkyl, and R'' being a $C_1$-$C_4$ alkyl.

The acylating agent thus is an acid halide, an ester, a simple anhydride, or a mixed anhydride. Alternatively, the compounds of the present invention can be made by condensation of N-aminoiminodibenzyl with appropriate 1-acyl-4-piperidone.

The most outstanding characteristic of the compounds of the present invention is their CNS depressant activity, which is totally unexpected from the disclosures of U.S. Pat. Nos. 3,373,168 and 3,457,271. While it is believed that this activity is related to the steric configuration of the compounds of the present invention, applicant does not wish to be bound by this theory. Nevertheless, the proposed structure of the compounds of the present invention is based on the following considerations:

a. reduction of a hexahydro compound (3) with boron hydride in tetrahydrofuran increases the molecular weight by 2, as found by mass spectroscopy — this means that two hydrogens have been added;

b. ultraviolet spectroscopy shows that the diphenylamine chromophore, constituted by rings C and E, and the nitrogen in position 14, is intact after the reduction — this means that the aromatic rings C and E have been preserved;

c. reductive cleavage of the $C_8$-$C_9$ bond, involving benzylic carbon atoms, is ruled out by both ultraviolet and nuclear magnetic resonance spectroscopy;

d. the only possibility left is the saturation of the $C_{4a}$-$C_{14a}$ double bond;

e. nuclear magnetic resonance spectroscopy of the prior art octahydro compounds suggests that they have the cis configuration.

The formation by the process of this invention of octahydroindolobenzazepines in which rings B and C constitute an indoline moiety is not only novel but also totally unexpected, especially in view of the results of a recent study of the reaction of indoles with diborane, Monti et al., Tetrahedron 27, 3331 (1971).

For the purpose of this specification and claims, the compounds of the present invention will be referred to as the trans- compounds to distinguish them from the compounds having the configuration of those described in U.S. Patents 3,373,168 and 3,457,271. This designation is used, however, with the understanding that if it is ultimately shown that either this isomer assignment is incorrect or an altogether different isomerism exists, the term "trans" as used herein still will designate the compounds having the configuration of the compounds specifically disclosed herein. The steric configuration of the compounds of the present invention can thus be characterized as that identical with one resulting when the $C_{4a}-C_{14a}$ double bond is reduced with the boron hydride/tetrahydrofuran complex.

The preparation of the compounds of the present invention is illustrated by the following examples, wherein all parts, proportions, and percentages are by weight unless otherwise indicated.

EXAMPLE 1 trans-1,2,3,4,4a,8,9,14a-Octahydro-3-methylpyrido[4',3':2,3]indolo[1,7-ab][1]benzazepine A solution of 4.76 g. of 1,2,3,4,8,9-hexahydro-3-methylpyrido[4',3':2,3]indolo[1,7-ab][1]benzazepine (which can be made according to the teachings of U.S. Pat. No. 3,457,271, Column 4, lines 27–54) in 50 ml. of tetrahydrofuran was added dropwise to a stirred 1N-solution of boron hydride in tetrahydrofuran (42 ml.) under a nitrogen blanket. After the addition was complete, the mixture was refluxed under nitrogen for five hours, then cooled in ice and quenched with 20 ml. of 6N hydrochloric acid. The mixture was distilled, the removed liquid being from time to time replaced by addition of dioxane. The mixture was again refluxed at 91°C. for one hour with additional 6N hydrochloric acid, then cooled to 70°C., made basic with sodium hydroxide, and evaporated in vacuum. The semisolid residue was treated with water and chloroform, and the chloroform layer was further worked up to yield 1.50 g. of a solid product, m.p. 128°–131°C. The mother liquors yielded an additional amount of material, m.p. 129.5°–130.5°C. Crystallization from ether raised the melting point to 132°–134°C.; UV spectrum: $\lambda_{max}^{CH_3OH}$ 279.5 m$\mu$ (log$\epsilon$ 4.13).

Reduction of 1,2,3,4,8,9,-hexahydro-3-methylpyrido[4',3':2,3]indolo[1,7-ab][1]benzazepine with sodium in liquid ammonia gave the prior art cis-octahydro compound, m.p. 120°–122°C; $\lambda_{max}^{CH_3OH}$ 287 m$\mu$ (log $\epsilon$ 4.08).

The trans-1,2,3,4,4a,8,9,14a-octahydro-3-methylpyrido[4',3':2,3]indolo[1,7-ab][1]benzazepine of the present invention can also be made by the following alternative route involving the reductive clevage of the 3-methoxymethylhexahydro compound as shown below.

A. A mixture of 2.74 g (0.01 mole) of 1,2,3,4,8,9-hexahydropyrido[4',3':2,3]indolo[1,7-ab][1]benzazepine, prepared as shown in section A of Example 2, and 75 ml of dry benzene was heated to boiling until solution occurred. Triethylamine (10.5 ml, 0.075 mole) was added to the warm solution, followed by dropwise addition of 2.0 ml (0.026 mole) of chloromethyl methyl ether. The resulting mixture was refluxed for 15 minutes, cooled to room temperature, and filtered. The filtrate gave on evaporation 3.05 g of a yellow oil, which was found by infrared spectroscopy to contain no free =NH groups.

B. The product of the preceding step (3.0 g, 0.01 mole) in 50 ml. of freshly purified tetrahydrofuran was added dropwise with stirring, under a nitrogen blanket, to 75 ml. of a 1M solution of boron hydride in tetrahydrofuran. The resulting mixture was refluxed under nitrogen for 26 hours; then it was cooled in ice and carefully decomposed with 50 ml of 5.5N hydrochloric acid. About 30 ml. of the liquid was removed by distillation, and 50 ml. of glacial acetic acid was added to redissolve the precipitate formed. The solution was refluxed for one hour, cooled to 55°–60°C., and made alkaline with 50% caustic. The product was recovered by extraction with ether, evaporation of the solvent, and column chromatography in benzene solution on basic alumina I. The pure product melted at 136°–138°C., and was identical with the material prepared by the first method described in Example 1.

EXAMPLE 2 trans-3-(Cyclopropylmethyl)-1,2,3,4,4a,8,9,14a-octahydropyrido[4',3':2,3]indolo[1,7-ab][1]benzazepine A. A mixture of 24.6 g of N-aminoiminodibenzyl (5-amino-10,11-dihydro-5H-dibenz[b,f]azepine) and 14.8 g. of 4-piperidone hydrochloride in 250 ml. ethanol was heated on a steam bath for 15 minutes and cooled; a solution of 20 g. of concentrated sulfuric acid in 250 ml. ethanol was added. The resulting mixture was reheated on the steam bath for additional 40 minutes; the solution which formed was cooled, basified with ammonia, and diluted with 1.1 of water. The crude, semisolid material which separated was taken up in ether, and the aqueous mother liquors were extracted with additional portions of ether. The combined etheral extracts were concentrated to 500 ml. and treated, under an atmosphere of nitrogen and with vigorous stirring, with 50 ml. of 5N hydrochloric acid. The resulting precipitate was filtered off, washed with ether and 1N hydrochloric acid, and dried in vacuo at 100° to yield 1,2,3,4,8,9-hexahydropyrido[4',3':2,3]indolo[1,7-ab][1]benzazepine hydrochloride, m.p. 309°, a salt only very slightly soluble in water. Dissolving the above salt in aqueous acetic acid, basifying with ammonia, filtering off the crude product and recrystallizing it from benzene regenerated the free 1,2,3,4,8,9-hexahydropyrido[4',3':2,3]indolo[1,7-ab][1]benzazepine.

B. To a solution of 16.4 g of 1,2,3,4,8,9-hexahydropyrido[4',3':2,3]indolo[1,7-ab][1]benzazepine in 500 ml. of dichloromethane, 7.3 g. of cyclopropanecarbonyl chloride was added, followed by dropwise addition of 10 ml. of triethylamine. A mildly exothermic reaction took place, after which stirring of the mixture was continued at room temperature overnight. The mixture was then washed with 1N hydrochloric acid and water and dried over anhydrous sodium carbonate. On evaporation to dryness, crude 3-(cyclopropylcarbonyl)-1,2,3,4,8,9-hexahydropyrido[4',3':2,3]indolo[1,7-ab][1]benzazepine (Formula 4; R' = cyclopropyl) was obtained as a glassy product. Recrystallization from ethanol yielded the pure material, m.p. 154°–156°C.

A solution of 8.6 g of the above compound in 120 ml. of tetrahydrofuran was added dropwise to a suspension of 2.3 g of lithium aluminum hydride in 180 ml. of tetrahydrofuran. On completion of the addition, the mixture was first refluxed for four hours, then allowed to stir at room temperature overnight and finally decomposed in the usual manner. After filtering off the inorganic salts, the filtrate was dried over anhydrous sodium carbonate and evaporated in vacuo; the residue was dissolved in a 1:1 mixture of ethyl acetate-benzene and chromatographed on a 14 × 2.2 cm. column of basic alumina, activity I. The eluate was taken down to dryness; the residual oil dissolved in absolute alcohol, saturated with ethanolic hydrogen chloride, and once again evaporated to dryness. Upon crystallization of the residue from acetone, trans-3-(cyclopropylmethyl)-1,2,3,4,8,9-hexahydropyrido[4′,3′:2,3]indolo[1,7-ab][1]benzazepine hydrochloride (Formula 3, R = cyclopropylmethyl), m.p. 267°, was obtained.

C. A solution of 9.25 g. of the free base of the above hexahydro compound in 75 ml. of tetrahydrofuran was reduced with 100 ml. of a 1M solution of boron hydride in tetrahydrofuran according to the method of Example 1. The title compound weighed 4.43 g. and had a melting point 152.5°–155°C.; U.V. spectrum $\lambda_{max}^{CH_3OH}$ 281 m$\mu$ (log $\epsilon$ 4.10). The hydrochloride salt melted at 273°–276°C.

Reduction of 3-(cyclopropylmethyl)-1,2,3,4,8,9-hexahydropyrido[4′,3′:2,3]indolo[1,7-ab][1]benzazepine with sodium in liquid ammonia gave the cis-product which formed a hydrochloride m.p. 241°–243°C., U.V. spectrum: $\lambda_{max}^{CH_3OH}$ 285 m$\mu$ (log $\epsilon$ 4.10).

The above two octahydro compounds were found to have different $R_f$ values in a thin layer chromatography system employing chloroform-butanol-28% aqueous ammonia in volume ratios 95:10:5, respectively, as solvent.

EXAMPLE 3 trans-3-(Cyclopropylmethyl)-1,2,3,4,4a,8,9,14a-octahydropyrido[4′,3′:2,3]indolo[1,7-ab][1]benzazepine (by a one-step reduction)

A solution of 100 g. of 3-(cyclopropylcarbonyl)-1,2,3,4,8,9-hexahydropyrido[4′,3′:2,3]indolo[1,7-ab][1]benzazepine in 500 ml. of tetrahydrofuran was added during a period of about 30 minutes to about 946 ml. (1 U.S. quart) of a 1M solution of boron hydride in tetrahydrofuran. The resulting solution was allowed to stand for 72 hours; then, a solution of 50 ml. of concentrated hydrochloric acid in 100 ml. of water was added, and the mixture was distilled until the pot temperature reached 100°C. The remaining material was cooled and diluted with 200 ml. of water and 75 ml. of 50% sodium hydroxide. The product was extracted with methylene chloride and was recovered as a crystalline material after treatment with acetone of the methylene chloride distillation residue. Yield 60.3 g., m.p. 146°–151°C. After recrystallization from methanol-chloroform 9:1 by volume, the melting point increased to 153°–155°C.

A sample of the above material was converted to the mesylate (methanesulfonate) salt, m.p. 227°–232°C.

EXAMPLE 4 trans-3-Ethyl-1,2,3,4,4a,8,9,14a-octahydropyrido[4′,3′:2,3]indolo[1,7-ab][1]benzazepine To a mixture of 9.0 g. of N-nitrosoiminodibenzyl, 12.4 g. of 1-acetyl-4-piperidone and 13.0 g. zinc dust in 75 ml. absolute ethanol there was added dropwise 24 ml. of glacial acetic acid with constant stirring and occasional cooling to keep the reaction temperature at 20°–25°C. After six hours, the unchanged zinc was filtered off and the mother liquor evaporated to near dryness. After extracting the residue with benzene, the extract was washed with saturated sodium chloride solution, dried over magnesium sulfate, and the solvent stripped off. The yellowish-brown residue was dissolved in 50 ml. ethanol, treated with a solution of 8 ml. concentrated sulfuric acid in 50 ml. ethanol, and heated on a steam bath for about ten minutes. On pouring into cold water, a gum separated, from which the aqueous layer was decanted. After dissolving the gum in ethyl acetate, the solution was washed with saturated sodium chloride solution and dried over sodium sulfate. Evaporation of the solvent gave a yellowish-white solid, which on crystallization from acetone yielded 3-acetyl-1,2,3,4,8,9-hexahydropyrido[4′,3′:2,3]indolo[1,7-ab][1]benzazepine as a white solid, m.p. 193°–196°C.

The above 3-acetyl compound was reduced with boron hydride in tetrahydrofuran according to the procedure of Example 3. The title compound was isolated, in a 36% yield, as its hydrochloride salt, m.p. 258°–260°C. (dec.); U.V.: $\lambda_{max}^{CH_3OH}$ 276 m$\mu$ (log$\epsilon$ 4.11).

Alternatively, the above compound can be made by reduction of the 3-acetyl compound under more drastic conditions, as follows:

A warm solution of the 3-acetyl compound (11.53 g., 0.0365 mole) in 300 ml. of diglyme is rapidly added dropwise to a mixture of 250 ml. of diglyme and 150 ml. of 1-molar boron hydride in tetrahydrofuran. The stirred mixture is then heated under nitrogen at 100°C. for twenty hours. The mixture is cooled to 20°C., decomposed with 75 ml. of 10N hydrochloric acid, and refluxed at 90°C. for one hour. It is cooled to 60°C., made alkaline with 100 ml. of 50% caustic, concentrated in vacuum, and extracted with chloroform. The chloroform extract yields a 67% yield of the 3-ethyl product.

EXAMPLE 5 trans-1,2,3,4,4a,8,9,14a-Octahydro-3-isobutylpyrido[4′,3′:2,3]indolo[1,7-ab][1]benzazepine 1,2,3,4,8,9-Hexahydro-3-isobutyrylpyrido[4′,3′:2,3]indolo[1,7-ab][1]benzazepine, m.p. 122°–124°, was made by a reaction of 1,2,3,4,8,9-hexahydropyrido[4′,3′:2,3]indolo[1,7-ab][1]benzazepine with isobutyryl chloride. This amide was reduced with boron hydride-tetrahydrofuran in diglyme in the manner described above as the alternate method of reducing the 3-acetyl compound to the 3-ethyl compound of Example 4.

The title compound was isolated as its hydrochloride addition salt, m.p. 286°–289°C. (dec.).

EXAMPLE 6 trans-3-Benzyl-1,2,3,4,4a,8,9,14a-octahydropyrido[4′,3′:2,3]indolo[1,7-ab][1]benzazepine Condensation of N-nitrosoiminodibenzyl with 1-benzyl-4-piperidone under conditions described in Example 4 for condensation with 1-acetyl-4-piperidinone gave 3-benzyl-1,2,3,4,8,9-hexahydropyrido[4′,3′:2,3]indolo[1,7-ab][1]benzazepine (hydrochloride, m.p. 200°C.). Reduction of the free base with boron hydride-tetrahydrofuran in diglyme under the conditions of the alternate method described in Example 4 for the reduction of the 3-acetyl compound gave an 84% yield of the title compound, which was isolated as its hydrochloride salt, m.p. 210°–212°C. (dec.). The free base was obtained by treating the hydrochloride salt in methanol solution with anhydrous ammonia. The free base melted at 146°–148°C.; U.V.: $\lambda_{max}^{CH_3OH}$ 279 m$\mu$ (log$\epsilon$ 4.13).

EXAMPLE 7 trans-1,2,3,4,4a,8,9,14a-Octahydro-3-(exo-7-norcaryl-methyl)pyrido[4',3':2,3]indolo[1,7-ab][1]benzazepine A solution of 7.05 g (0.0178 mole) of 1,2,3,4,8,9,-hexahydro-3-[(exo-7-norcaryl)carbonyl]pyrido[4',-3':2,3]indolo[1,7-ab][1]benzazepine, which was made from 1,2,3,4,8,9-hexahydropyrido[4',3':2,3]indolo[1,7-ab][1]benzazepine and (exo-7-norcaryl)carbonyl chloride, in 100 ml of diglyme was added dropwise in a nitrogen atmosphere to a stirred mixture of 100 ml of 1M boron hydride in tetrahydrofuran and 400 ml of diglyme. The mixture was heated at 110°C for twenty-three hours and cooled to about 20°C. Hydrochloric acid, 75 ml of 10N HCl, was added; the mixture was refluxed at 100°C for one hour, cooled to about 60°C, and made basic with 100 ml of 50% NaOH.

The product was isolated and purified by several extraction and recrystallization steps. Its m.p. was 186°–187°C.

Additional representative compounds of Formula (2) which can be made by the above-described process are listed below:

1. trans-3-cyclohexylmethyl-1,2,3,4,4a,8,9,14a-octahydropyrido[4',3':2,3]indolo[1,7-ab][1]benzazepine hydrochloride, m.p. 180°C. (dec.)
2. trans-3-cyclopentylmethyl1,2,3,4,4a,8,9,14a-octahydropyrido[4',3':2,3]indolo[1,7-ab][1]benzazepine hydrochloride, m.p. 263°C. (dec.)
3. trans-3-cyclopropyl-1,2,3,4,4a,8,9,14a-octahydropyrido[4',3':2,3]indolo[1,7-ab][1]benzazepine hydrochloride
4. trans-3-(1-adamantylmethyl)-1,2,3,4,4a,8,9,14a-octahydropyrido[4',3':2,3]indolo[1,7-ab][1]benzazepine hydrochloride
5. trans-3-(2-adamantylmethyl)-1,2,3,4,4a,8,9,14a-octahydropyrido[4',3':2,3]indolo[1,7-ab][1]benzazepine hydrochloride
6. trans-3-(cis-2,3-dimethylcyclopropyl)methyl-1,2,3,4,4a,8,9,14a-octahydropyrido[4',3':2,3]indolo[1,7-ab][1]benzazepine hydrochloride
7. trans-1,2,3,4,4a,8,9,14a-octahydro-3-(4-methylbicyclo[2.2.2]oct-1-yl)methylpyrido[4',3':2,3]indolo[1,7-ab][1]benzazepine hydrochloride
8. trans-1,2,3,4,4a,8,9,14a-octahydro-3-[(1-methyl pyrido[4',3':2,3]indolo[1,7-ab][1]benzazepine hydrochloride
9. trans-3-[(bicylo[[2.2.1]hept-2-yl)methyl]-1,2,3,4,4a,8,9,14a-octahydropyrido[4',3';2,3]indolo[1,7-ab][1]benzazepine hydrochloride
10. trans-3-furfuryl-1,2,3,4,4a,8,9,14a-octahydropyrido[4',3':2,3]indolo[1,7-ab][1]benzazepine hydrochloride
11. trans-3-(4-chlorobenzyl)-1,2,3,4,4a,8,9,14a-octahydropyrido[4',3':2,3]indolo[1,7-ab][1]benzazepine hydrochloride
12. trans-3-(2-methoxybenzyl)-1,2,3,4,4a,8,9,14a-octahydropyrido[4',3':2,3]indolo[1,7-ab][1]benzazepine hydrochloride
13. trans-3-[3-(2-chlorophenyl)propyl]-1,2,3,4,4a,8,9,14a-octahydropyrido[4',3':2,3]indolo[1,7-ab][1]benzazepine hydrochloride
14. trans-3-[3-(4-bromophenyl)propyl]-1,2,3,4,4a,8,9,14a-octahydropyrido[4',3':2,3]indolo[1,7-ab][1]benzazepine hydrochloride
15. trans-1,2,3,4,4a,8,9,14a-octahydro-3-[3-(3-methoxyphenyl)propyl]pyrido[4',3':2,3]indolo[1,7-ab][1]benzazepine hydrochloride
16. trans-3-cycloheptylmethyl-1,2,3,4,4a,8,9,14a-octahydropyrido[4',3':2,3]indolo[1,7-ab][1]benzazepine hydrochloride
17. trans-1,2,3,4,4a,8,9,14a-octahydro-3-phenethyl-pyrido[4',3+:2,3]indolo[1,7-ab][1]benzazepine, m.p, 270°C. (dec.)
18. trans-1,2,3,4,4a,8,9,14a-octahydro-3-(3-phenylvpropyl)pyrido[4',3':2,3]indolo[1,7-ab][1]benzazepine
19. trans-1,2,3,4,4a,8,9,14a-octahydro-3-(2-thenyl)-pyrido[4',3':2,3]indolo[1,7-ab][1]benzazepine
20. trans-1,2,3,4,4a,8,9,14a-octahydro-3-pentyl-pyrido[4',3':2,3]indolo[1,7-ab][1]benzezepine
21. trans-1,2,3,4,4a,8,9,14a-octahydro-3-neopentyl-pyrido[4',3':2,3]indolo[1,7-ab][1]benzazepine
22. trans-1,2,3,4,4a,8,9,14a-octahydro-3-[(2-methyl-cyclopropyl)methyl]pyrido[4',3':2,3]indolo[1,7-ab][1]benzazepine hydrochloride The compounds of the present invention can be administered to warm-blooded animals as CNS depressants analgesics either in the form of free bases or of their addition salts with pharmaceutically acceptable organic or inorganic acids. The salts often are more water-soluble than the free bases and thus are more suitable in preparations in which solubility is important, for example, in injectable solutions. Representative pharmaceutically acceptable acids which can be used to form 1,2,3,4,4a,8,9,14a-octahydro-3-(substituted)-pyrido[4',3':2,3]indolo[1,7-ab][1]benzazepine derivative salts of the present invention are: hydrochloric, hydrobromic, sulfuric, sulfamic, phosphoric, nitric, maleic, fumaric, benzoic, ascorbic, citric, pamoic, succinic, methanesulfonic; ethanedisulfonic, acetic, oxalic, propionic, tartaric, salicylic, gluconic, lactic, malic, mandelic, cinnamic, citraconic, aspartic, stearic, palmitic, itaconic, glycolic, p-aminobenzoic, glutamic, and toluenesulfonic acids.

It is an important characteristic of the compounds of the present invention that they not only have a different steric configuration from that of the 3-substituted prior art octahydro compounds but also have distinct biological activities which distinguish these new compounds from both the prior art octahydro compounds and the corresponding hexahydro compounds. The CNS activity of the compounds of the present invention can be evaluated by one or more of the following tests:

Primary Rodent Screens

Decreased Locomotor Activity (L.M.A.)

Results given in:
mg/kg po/mouse
mg/kg po/rat

This reaction sign is measured subjectively by observing how an animal behaves when it is removed from an observation cage and placed on a table top. Untreated animals will immediatedly begin active exploration of their environment. Animals that have received a depressant compound will show a gradually decreasing responsiveness to a new environment. The degree of stimulation by the observer needed to produce active locomotion is rated on an arbitrary scale. This ranges from a score of −1 where only a slight touch of the animal's body is required to a −4 where the animal is unresponsive or minimally responsive to the application of a pain stimulus (pressure at the base of the tail). The minimal effective dose (MED) is the lowest oral dose producting an obvious decrease of locomotor activity (with a score of at least −1). Groups of 3 mice are given decreasing oral doses at 0.5 log intervals (300, 100, 30. . .etc.) until no behavioral effects are evident. Decrease of locomotor activity is indicative of general central nervous system depressant activity.

Ptosis
 Results given in:
 mg/kg po/mouse
 mg/kg po/rat

Degree of eyelid closure is used as a measure of central nervous system depression. An animal is removed from its observation cage and allowed to remain outside the cage for 30 seconds. At the end of this time a rating of degree of eyelid closure is made on an arbitrary scale. Passive ptosis, i.e., eye closure that can be temporarily reversed by handling, is generally indicative of sedative activity for a psychotropic compound. (Active ptosis, i.e., eyelid closure that remains unchanged with handling is generally suggestive of α-adrenergic blocking activity. It is a relatively rarely seen phenomenon.) Only passive ptosis was observed for these compounds, the MED for which is reported.

Catalepsy
 Results given in:
 mg/kg po/mouse
 mg/kg po/rat

The ability of an animal to remain in an abnormal position is used as another indication of central nervous system depressant activity. A test animal is removed from its observation cage and positioned so that its hind legs are on the table top and its front legs rest on the side of the observation cage. If an animal maintains this position for at least 10 seconds, it is considered to be showing cataleptic behavior.

Secondary Evaluation Tests
Tetrabenazine Antagonism (T.B.Z.A.)
 Results given in:
 mg/kg po/mouse
 mg/kg po/rat The tetrabenazine (TBZ) antagonism test is used to test for potential antidepressant-like activity in rodents. One hour after oral administration of a test compound, a 40 mg/kg dose of TBZ is given subcutaneously. Thirty minutes after TBZ administration, the mice are placed in the center of a circle; the diameter of the circle is twice the body length of the mouse or rat. After 30 seconds, a reading is made of the degree of ptosis and whether the animal has moved out of the circle. Animals that have received only TBZ will show marked ptosis and immobility. Tricyclic antidepressants of the imipramine type will antagonize the ptosis but not the immobility. Antidepressants of the amphetamine or monoamine oxidase inhibitory type will antagonize both the ptosis and immobility induced by TBZ. The $ED_{50}$ is the dose producing antagonism of TBZ-induced ptosis, but not of TBZ-induced immobility, in 50% of the animals.

Rat Conflict (Approach-Avoidance) Test (Conflict)
 Results given in: mg/kg po/rat Food deprived rats are trained to pass from one compartment to an adjacent one to obtain food. The training consists of 3 exposures to the test situation on day one of the experiment. The rats are given limited (1–2 hr) free access to food in their home cages on day one and are then food deprived for at least 18 hours. On day two of the experiment, the rats are given a control exposure to the test situation followed by a second exposure after one-half to 1 hour in which they are shocked after crossing and eating. Groups of 6–8 rats are then dosed orally with solvent or test compound and then re-exposed to the test situation after 1 or 2 hours.

Compounds showing minor tranquilizer (anxiolytic) activity in man such as diazepam and meprobamate produce an apparent decreased fear in the test animals so that they cross to obtain food despite having received a shock earlier. This effect is dose-related (and the MED is the minimum dose at which this effect is obtained); rats dosed with solvent only consistently show a high level of fear as evidenced by decreased mobility and absence of feeding when placed in the test situation after receiving a shock.

Mouse and Rat Conditioned Avoidance Response (C.A.R.):
 Results given in:
 mg/kg po/mouse
 mg/kg po/rat Mice and rats are trained to jump out of a pit onto a ledge to avoid shock when presented with a light and sound conditioned stimulus. The animals are tested 1, 2, and 4 hours after administration of the test compound. Three to four dose levels and groups of 4–8 animals/dose are used. The $ED_{50}$ is the dose producing a block of the C.A.R. in 50% of the animals. Blocking of the C.A.R. at non-toxic doses appears to correlate with major tranquilizer activity in man.

Dog Conditioned Avoidance Response (C.A.R.):
 Results given in: mg/kg po/dog

Dogs are trained to raise a forelimb when presented with a conditioned stimulus (light) in order to avoid an electric shock. Blocks of 10 trials are given to groups of 4 dogs during a pretreatment period and at 1, 2, and 4 hours after oral administration of the test compound. The $ED_{50}$ values are calculated as the dose causing 50% of the animals to show 5 or more incorrect responses. Blocking of the C.A.R. at non-toxic doses appears to correlate with major tranquilizer activity in man.

Rhesus Monkey Taming Effects (Taming):
 Results given in: mg/kg po/monkey

Compounds are administered orally to groups of 6 rhesus monkeys. The behavior of the animals is then evaluated by observational means. Taming effects are determined by the ability of the observer to approach and touch the monkey. Compounds with major tranquilizer activity in man can produce a state of passive tameness in the rhesus monkey wherein it can be touched without provoking any of the threatening or aggressive behavior seen in the normal animal. The MED is the minimal oral dose at which some taming effect can be observed.

The compounds of the present invention have been compared in the above tests with the corresponding hexahydropyridoindolobenzazepines as well as with the prior art 3-methyl and 3-ethyl octahydro compounds. For better identification, the prior art compounds are designated "octahydro cis", while the present compounds are designated "octahydro trans". The results are presented in the following Tables I and II:

TABLE I

3-R-1,2,3,4,8,9-HEXAHYDRO- and 1,2,3,4,4a,8,9,14a-OCTAHYDRO-
PYRIDO[4',3':2,3]INDOLO[1,7-ab][1]BENZAZEPINES

| R | Series | Primary Rodent Screens | | | | | |
|---|---|---|---|---|---|---|---|
| | | L.M.A. (mouse) MED | L.M.A. (rat) MED | Ptosis (mouse) MED | Ptosis (rat) MED | Catalepsy (mouse) MED | Catalepsy (rat) MED |
| methyl | hexahydro | 10 | 30 | 30 | 30 | 300 | 100 |
| | octahydro cis | 30 | 30 | >300 | | >300 | >300 |
| | | | | | S300 | | |
| | 1 octahydro trans | 3 | 1 | 10 | 10 | 10 | 3 |
| ethyl | hexanhydro | 30 | 30 | 30 | | >300 | >300 |
| | | | | | S300 | | |
| | 4 octahydro trans | 1 | 1 | 10 | 10 | 30 | 10 |
| (cyclopropylmethyl) | hexahydro | 10 | 10 | 30 | 30 | 30 | 30 |
| | 2 octahydro trans | 3 | 1 | 10 | 3 | 3 | 3 |
| isobutyl | hexahydro | ~60 | * | ~60 | * | ~60 | * |
| | octahydro trans | 2 | 4 | 8 | 5 | 2 | 6 |
| benzyl | hexahydro | ~200 | >300 | >300 | | >300 | >300 |
| | | | | | S300 | | |
| | octahydro trans | 2 | 65 | 13 | 150 | 49 | >300 |
| norcarylmethyl | hexahydro | 10 | 1 | 10 | 10 | >300 | >300 |
| | octahydro | 3 | 3 | 3 | 3 | 3 | 300 |

* not available

TABLE II

3-R-1,2,3,4,8,9-HEXAHYDRO- and 1,2,3,4,4a,8,9,14a-OCTAHYDRO-
PYRIDO[4',3':2,3]INDOLO[1,7-ab][1]BENZAZEPINES

| R | Series | Secondary Evaluation Tests | | | | | | |
|---|---|---|---|---|---|---|---|---|
| | | T.B.Z.A. (mouse) $ED_{50}$ | T.B.Z.A. (rat) $ED_{50}$ | Conflict (rat) MED | C.A.R. (mouse) $ED_{50}$ | C.A.R. (rat) $ED_{50}$ | C.A.R. (dog) $ED_{50}$ | Taming (monkey) MED |
| methyl | hexahydro | >100 | >100 | 20 | 20 | 30 | >30 | 10 |
| | octahydro cis | 15 | 7.4 | >40 | >40 | >40 | >30 | >20 |
| | 1 octahydro trans | >100 | >100 | >40 | ~10 | ~10 | ~10 | 1 |
| ethyl | hexahydro | >100 | >100 | 20 | >40 | >40 | >30 | >20 |
| | 4 octahydro trans | >100 | >100 | >40 | ~10 | ~10 | ~6 | 1 |
| (cyclopropylmethyl) | hexahydro | >100 | >100 | 10 | 20 | 40 | >30 | 3 |
| | 2 octahydro trans | >100 | >100 | >40 | 0.7 | 0.7 | 3 | 1 |

It can be seen from the above experimental data that none of the hexahydro compounds tested nor the single cis-octahydro compound tested had a dose-related effect on conditioned responding (C.A.R.) in the dog at oral doses up to 30 mg/kg, while all three trans-octahydro compounds had such an effect at doses of 10 mg/kg or lower. The CNS depressant activity of the trans-series was substantially greater than that of the cis-series or of the hexahydro compounds in the great majority of cases, as can be seen from all primary rodent screen results and from the C.A.R. and taming secondary tests.

The antidepressant activity of the cis-octahydro compounds, disclosed in the U.S. Pat. Nos. 3,373,168 and 3,457,271 patents, was not found in either the trans-series or the hexahydro series, as can be seen in the T.B.Z.A. tests in mice and rats. The anxiolytic activity of the hexahydro compounds, disclosed in the copending application Ser. No. 170,990 of Michael Finizio, was not found in either the cis- or the trans-octahydro compounds in the diagnostic rat conflict test.

This characteristic CNS activity pattern of the trans-compounds of the present invention is completely unexpected from prior art since it differs both qualitatively and quantitively from the CNS activity profile of the prior art cis-compounds.

The analgesic activity of the compounds of the present invention is conveniently determined in a phenyl-quinone writhing test, as described below:
Phenylquinone Writhing (P.Q.W.):
  results given in: mg/kg po/mouse Groups of at least 10 mice are given phenyl-p-benzoquinone 2.5 mg/kg intraperitoneally 30 minutes after oral administration of graded doses of the test substance. Two or more dose levels are used for each compound. For scoring purposes, a "writhe" is defined as stetching, twisting of a hindleg inward, or contraction of the abdomen. The total number of writhes for each animal, treated and control animals side-by-side, are counted over a 30-minute time interval. An $ED_{50}$, calculated on basis of the percentage of animals at each dose level which showed 50% or less of the average number of writhes of the control animals, is reported for each compound submitted to this screening test. The PQW test is widely used as an indicator of potential analgesic activity in man, especially for non-narcotic substances.

The results obtained with the compounds of this invention are presented in the Table below, in which codeine and aspirin are used as the standard analgesics for comparison.

| Phenylquinone Writhing Screen | |
|---|---|
| trans-3,R,1,2,3,4,4a,8,9,14a-OCTAHYDRO-PYRIDO[4',3':2,3]INDOLO[1,7-ab][1]BENZAZEPINES | |
| R | P.Q.W. (mouse) $ED_{50}$ |
| methyl | 1.9 |
| ethyl | 0.40 |
| (cyclopropylmethyl) | 2.3 |
| isobutyl | 1.75 |
| benzyl | 28 |
| (exo-7-norcarylmethyl) | 14 |
| phenethyl | 4.7 |
| cyclopentylmethyl | 2.0 |

-continued

Phenylquinone Writhing Screen trans-3,R,1,2,3,4,4a,8,9,14a-OCTAHYDRO-
PYRIDO[4',3':2,3]INDOLO[1,7-ab][1]BENZAZEPINES

| R | P.Q.W. (mouse) $ED_{50}$ |
|---|---|
| cyclohexylmethyl | 13 |
| Standard Compounds | |
| codeine | 19 |
| aspirin | 94 |

The free amines of formula 2 and some of their pharmaceutically acceptable inorganic or organic acid addition salts are substantially insoluble in water. As CNS depressants, they are best administered orally at a level of about 0.1 to about 10 milligrams per kilogram of body weight of the animal. Some addition salts of the compounds having formula 2 are more water-soluble and can be administered by subcutaneous or intramuscular injection. The dosage employed in such cases generally would be within the range of about 0.02 to about 5 milligrams per kilogram of body weight.

As analgesics, the compounds of this invention are administered orally at a level of about 0.1–10 mg/kg or parenterally at the rate of about 0.05–5 mg/kg of body weight.

The compounds of the present invention can be formulated into compositions comprising a compound of formula 2 or a pharmaceutically acceptable acid addition salt thereof together with a pharmaceutically acceptable carrier. The carrier may be either a solid or liquid, and the compositions can be in form of tablets, liquid-filled capsules, dry filled capsules, aqueous solutions, non-aqueous solutions, suppositories, syrups, suspensions, and the like. The compositions can, and in many cases do contain suitable preservatives, coloring and flavoring agents. Some examples of the carriers which can be used in the preparation of the products of the invention are gelatin capsules, sugars such as lactose and sucrose, starches, dextrans and cellulosics, such as methyl cellulose and cellulose acetate phthalate, gelatin; talc; stearic acid salts; vegetable oils such as peanut oil, cottonseed oil, sesame oil, olive oil, corn oil and oil of theobroma; liquid petrolatum; polyethylene glycol; glycerine; sorbitol; propylene glycol; ethanol; agar; water and isotonic saline.

In preparing the compositions of the invention for pharmaceutical uses, the conventional practices and precautions are used. The composition intended for parenteral administration must be sterile, and this can be accomplished either by using sterile ingredients and carrying out the production under aseptic conditions, or by sterilizing the final composition by one of the usual procedures such as autoclaving under appropriate temperature and pressure conditions. Customary care should be exercised that no imcompatible conditions exist between the active components and the diluent preservative or flavoring agent or in the conditions employed in preparation of the compositions.

The compositions of the invention can be introduced into warm-blooded animals by the oral, rectal or parenteral route. This can be done by swallowing, in the case of liquid or solid preparations; by suppositories; or by injecting the liquid preparations intravenously, intramuscularly, intraperitoneally, or subcutaneously.

The compounds of this invention are administered to warm-blooded animals to produce the desired pharmacologic response. Dosage forms are prepared at various strengths depending on the potency of the compound and the desired effect. It is possible, for example, to estimate the probable human dose for analgesia by comparing the animal analgetic dose for the compound of this invention to the dose of a standard drug in the same animal system. Thus, the compound of Example 1 is shown to have analgesic activity compared to codeine phosphate.

| | Analgesic $ED_{50}$ | Usual Human Dose | Dosage Form Strength |
|---|---|---|---|
| Codeine phosphate | 19 mg/kg | 15–300 mg/day | 15–60 mg |
| Compound of Example 1 | 1.9 mg/kg | 1.5–30 mg/day | 1.5–6 mg |

Since the compound of Example 1 is about 10X more potent than codeine phosphate its human dose is estimated to be 1.5–30 mg/day (1/10 the codeine dose). Dosage forms of the compound will ordinarily contain 1.5 to 6 mg of the active ingredient, however lower or higher strengths may be required depending on the age and condition of the patient being treated, the severity of the pain and the frequency of treatment required.

In a similar manner, by comparing the effects of a standard drug like chlorpromazine in the same animal systems as the compounds of this invention, the strengths of dosage forms for human use may be determined.

| | LMA* | Cata-* lepsy | Ptosis* | Usual Human Dose | Dosage Form Strength |
|---|---|---|---|---|---|
| Chlorpromazine | 5 | 6 | 6 | 10–1000 mg/day | 10–200 mg |
| Compound of Example 5 | 4 | 6 | 5 | 10–1000 mg/day | 10–200 mg |

*$ED_{50}$

Since the compound of Example 5 is similar in potency to chlorpromazine in animal tests, the human dose range is estimated to be similar to that recommended for chlorpromazine. The human dose range for other compounds of the invention can be estimated in the same way.

Typical formulations of the type listed above which may be used for the administration of these compounds are:

| Example A Ingredients | mg./tablet |
|---|---|
| 3-(benzyl)-1,2,3,4,4a,8,9,14a-octa hydropyrido[4',3':2,3]indolo[1,7-ab][1]benzazepine | 15 mg. |
| lactose, USP | 183 mg. |

All of the above ingredients are passed through a suitable sieve, blended for 20 minutes, and compressed directly into tablets of 200 mg. on a suitable tablet press using a 11/32" punch and die.

-continued

| Example B Ingredients | mg./tablet |
|---|---|
| 1,2,3,4,4a,8,9,14a-octahydro-3-methylpyrido[4',3':2,3]indolo[1,7-ab][1]benzazepine hydrochloride | 50 mg. |
| lactose, USP | 215 mg. |
| methylcellulose, USP | 15 mg. |
| talc, USP | 6 mg. |
| starch, USP | 10 mg. |
| magnesium stearate, USP | 4 mg. |
| color (if desired) | q.s. |

The lactose and active ingredient are wet granulated with a solution of methylcellulose in a blender until a satisfactory mass is achieved. The mass is dried and classified through an appropriate sieve. The remaining ingredients are passed through an 80 mesh sieve and blended with the dried granulated material. The blend is then compressed into tablets on a suitable tablet press at a weight of 300 mg. using a ⅜inch punch and die.

| Example C Ingredients | mg./capsule |
|---|---|
| 3-ethyl-1,2,3,4,4a,8,9,14a-octahydropyrido[4',3':2,3]indolo[1,7-ab][1]benzazepine | 25 mg. |
| lactose, USP | 100 mg. |
| magnesium stearate, USP | 1 mg. |
| colloidal silicon dioxide, N.F. | 2 mg. |

The combined ingredients are blended and passed through a 40 mesh sieve, and the mixture is encapsulated into a two-piece hard gelatin no. 3 capsule on a suitable encapsulating machine at a net weight of 128 mg.

| Example D Ingredients | gram/liter |
|---|---|
| 3-(cyclopropylmethyl)-1,2,3,4,4a,8,9,14a-octahydropyrido[4',3':2,3]indolo[1,7-ab][1]benzazepine methanesulfonate | 3 g. |
| granulated sugar | 600 g. |
| sodium benzoate | 1 g. |
| flavor | q.s. |
| color | q.s. |
| deionized water | q.s. |

All of the above ingredients are dissolved in water and made up to a volume of one liter.

| Example E Ingredients | gram/liter |
|---|---|
| 3-(cyclopropylmethyl)-1,2,3,4,4a,8,9,14a-octahydropyrido[4',3':2,3]indolo[1,7-ab][1]benzazepine methanesulfonate | 10 g. |
| propylparaben, USP | 0.2 g. |
| methylparaben, USP | 1.8 g. |
| Water for Injection | q.s to 1 liter |

Dissolve the parabens in about 800 ml. of Water for Injection at 80°. Cool to room temperature, add the active ingredient, and stir to dissolve. If the solution is aseptically prepared, sterile filtration through a millipore filter or other suitable retentive filter is desirable. Terminal sterilization by autoclaving may also be employed to render the product sterile.

For the purpose of the present invention, the expression "consisting essentially" appearing in the composition claims means that, in addition to the ingredients specifically recited in the claims, other ingredients also can be present, provided they do not adversely affect the operability of the compositions for their intended use.

I claim:

1. A tranquilizer composition consisting essentially of a pharmaceutically acceptable carrier and an effective amount of a compound of the following formula:

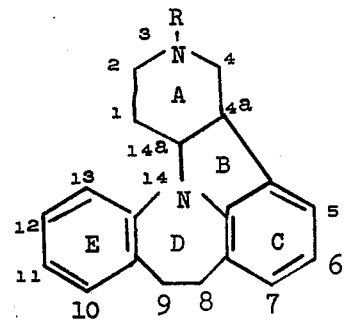

wherein
R is benzyl; benzyl ring-substituted with methyl, methoxy, or chloro; phenethyl; 3-phenylpropyl; 3-phenylpropyl ring-substituted with chloro, bromo, or methoxy; furfuryl; 2-thenyl; $C_1$–$C_5$ alkyl; cyclopropyl; $C_4$–$C_8$ cycloalkylmethyl; (methycyclopropyl)methyl; exo-7-norcarylmethyl; (4-methylbicyclo[2.2.2]oct-1-yl)methyl; (bicyclo[2.2.1]hept-2-yl)methyl; 1-adamantylmethyl or 2-adamantylmethyl;
and the hydrogens in the 4a and 14a positions are in trans relationship to each other; or a pharmaceutically acceptable addition salts of these free amines.

2. A method of producing a tranquilizer effect in a warm-blooded animal, said method comprising administering to said animal an effective amount of a compound selected from the group consisting of:
A. a free amine having the following formula

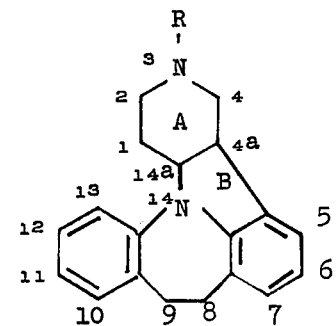

wherein
R is benzyl; benzyl ring-substituted with methyl, methoxy, or chloro; phenethyl; 3-phenylpropyl; 3-phenylpropyl ring substituted with chloro, bromo, or methoxy; furfuryl; 2-thenyl; $C_1$–$C_5$ alkyl; cyclopropyl; $C_4$–$C_8$ cycloalkylmethyl; (methylcyclopropyl)methyl; exo-7-norcarylmethyl; (4-methylbicyclo[2.2.2]oct-1-yl)methyl; (bicyclo[2.2.1]hept-2-yl)methyl; 1-adamantylmethyl or 2-adamantylmethyl;

and the hydrogens in the 4a and 14a positions are in trans relationship to each other; and B. an addition salts of a free amine of A, above, with a pharmaceutically acceptable acid.

3. The method of claim 2 wherein the active compound is administered orally at a level of about 0.1–10 milligrams per kilogram of body weight of the animal.

4. The method of claim 2 wherein the active compound is a water-soluble salt of paragraph B of claim 2, and it is administered to the warm-blooded animal by a subcutaneous or intramuscular injection at a rate of about 0.02–5 milligrams per kilogram of body weight of the animal.

* * * * *